(12) United States Patent
Koistinen et al.

(10) Patent No.: US 6,362,362 B1
(45) Date of Patent: Mar. 26, 2002

(54) PROCESS FOR PREPARING AND PURIFYING COMPLEX ESTERS

(75) Inventors: Jari Koistinen, Jyväskylä; Kari Rissanen, Hankasalmi; Salme Koskimies, Helsinki, all of (FI)

(73) Assignee: Fortum Oil & Gas Oy, Espoo (FI)

( * ) Notice: Subject to any disclaimer, the term of this patent is extended or adjusted under 35 U.S.C. 154(b) by 0 days.

(21) Appl. No.: 09/402,329

(22) PCT Filed: May 7, 1998

(86) PCT No.: PCT/FI98/00391

§ 371 Date: Oct. 4, 1999

§ 102(e) Date: Oct. 4, 1999

(87) PCT Pub. No.: WO98/50338

PCT Pub. Date: Nov. 12, 1998

(30) Foreign Application Priority Data

May 7, 1997 (FI) .................................................. 971973

(51) Int. Cl.⁷ .............................................. C07C 67/00
(52) U.S. Cl. ........................ 560/199; 560/198; 560/263
(58) Field of Search ................................ 560/198, 263, 560/199

(56) References Cited

U.S. PATENT DOCUMENTS

| | | | | |
|---|---|---|---|---|
| 2,710,877 A | * | 6/1955 | Young et al. ............... | 260/485 |
| 2,780,644 A | * | 2/1957 | Ready ......................... | 260/485 |
| 2,815,368 A | * | 12/1957 | Matuszak .................... | 260/484 |
| 4,405,471 A | | 9/1983 | Manson et al. | |

FOREIGN PATENT DOCUMENTS

| DE | 1 056 597 | * | 5/1959 |
|---|---|---|---|
| WO | 9116296 | | 10/1991 |

OTHER PUBLICATIONS

"Statistical Study of Hydrolytic Stability in Amine–Neutralized Waterborne Polyester Resins as a Function of Monomer Composition" Journal of Coatings Technology. Jones, T.; Mccarthy J.M. vol. 67(844) (1995).*

* cited by examiner

*Primary Examiner*—Gary Geist
*Assistant Examiner*—Zachary C. Tucker
(74) *Attorney, Agent, or Firm*—Birch, Stewart, Kolasch & Birch, LLP

(57) ABSTRACT

The invention concerns a process for manufacturing polyol complex esters. According to the method, a polyol, such as BEPD or NPG, is reacted with mono- and polyvalent acids in the presence of a catalyst to produce a reaction blend containing complex esters. According to the invention the acid components of the reaction blend are neutralized with a tertiary amine, and the complex esters are recovered from the thus treated reaction blend. The basic amines that are used form salt-like compounds with the carboxylic acids. The compounds enter the aqueous phase, from which they are easily separated, whereby the complex esters are recovered with high yield.

28 Claims, 2 Drawing Sheets

PROCESS FOR PREPARING AND PURIFYING COMPLEX ESTERS

Figure 1:
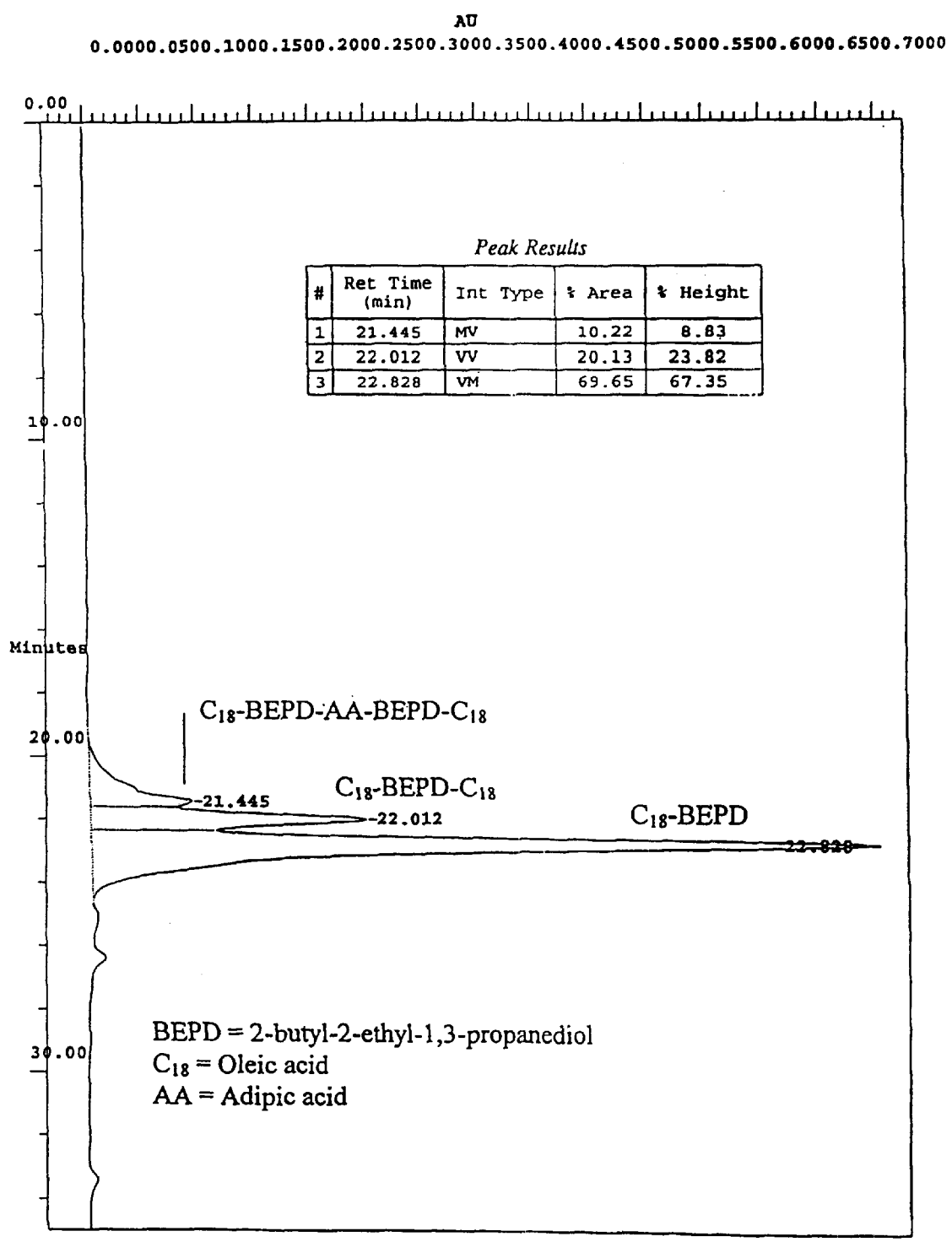
Figure 2:
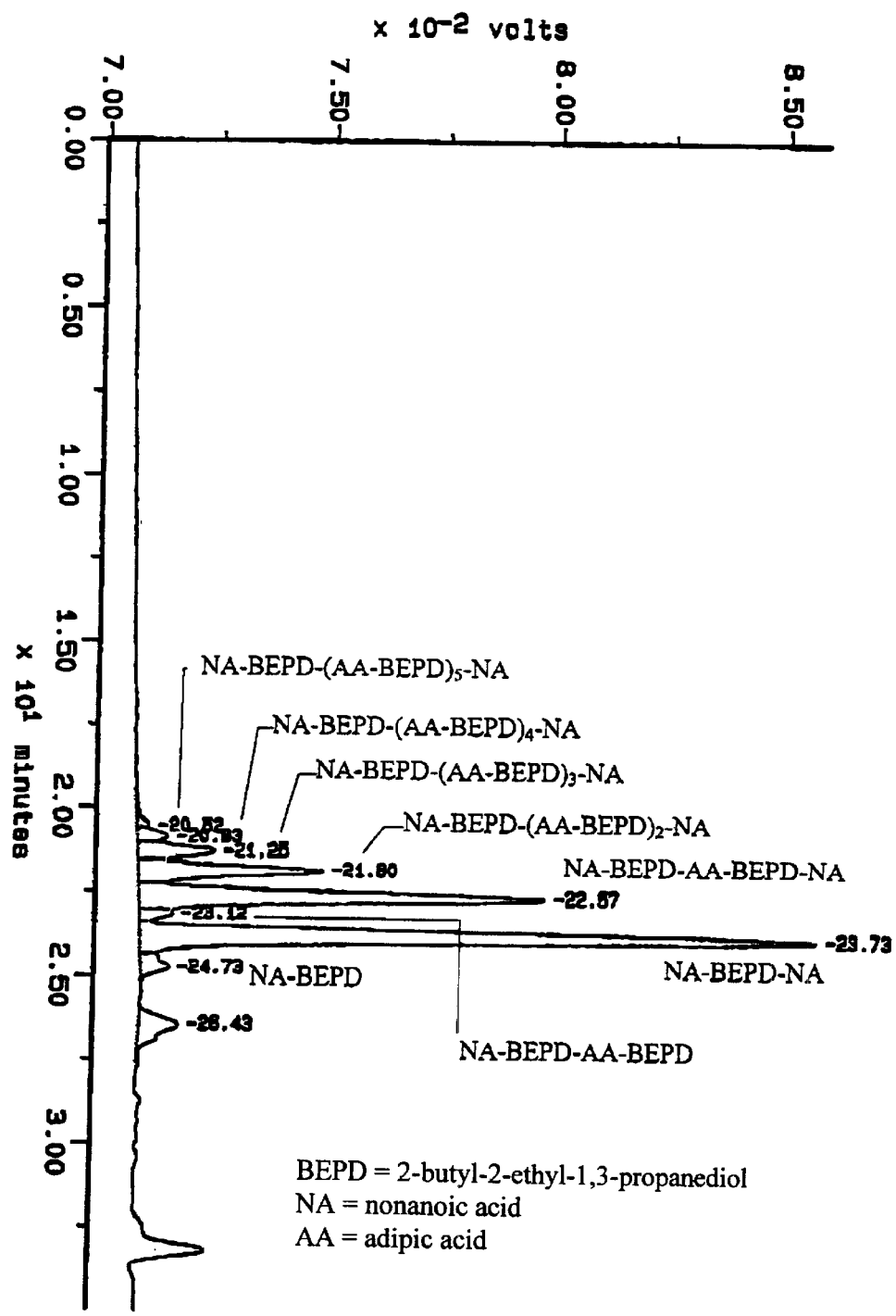

This application is the national phase under 35 U.S.C. §371 of PCT International Application No. PCT/FI98/00391 which has an International filing date of May 7, 1998 which designated the United States of America.

The present invention concerns a process according to the preamble of claim 1 for the preparation and purification of complex polyol esters.

According to the process, a mixture of complex esters is made by reacting a polyol with mono- and polybasic acids in the presence of a catalyst, the reaction mixture is treated with a base to neutralize the acid components, and the complex esters are retrieved from the thus treated reaction mixture.

Complex polyol esters can be used as lubricant base stocks, which can serve as complete lubricants, or as compounded lubricants with, e.g., hydrocarbon lubricants, to improve the biodegradability of said products, as biodegradable hydraulic oils, compressor oils, metal working fluids, and with chlorine-free, fluorine-containing refrigerants as the fluid lubricant component in refrigerator compressors.

The general manufacturing of polyol esters is known A considerable problem is, however, the purification of the final products, especially the removal of acid impurities (the carboxylic acids that did not react), because many methods used for neutralizing and extraction give rise to emulsions that are difficult to separate. Strong inorganic bases, i.e. sodium hydroxide, or basic salts, i.e. sodium carbonate or sodium bicarbonate, are usually used in the neutralizing process. Also hot-neutralizing methods are known. The strong bases decompose the desired ester product and cause the formation of emulsions. Various difficult steps of refining and distillation are needed after neutralization, as mentioned for example in SE Patent Application No. 7400019-1.

The technical solution described in the DE Published Patent Application No. 1 444 851 can be mentioned as an example of the prior art: a raw ester product originating in complex esterification of trimethylpropane is first diluted with petrol ether, after which it is washed with a 5% aqueous solution of sodium hydroxide to neutralize the remaining acid. Washing is continued with a 12% sodium chloride solution until the mixture is neutral. Active carbon is subsequently added, and then the mixture is heated at low pressure to 160–180° C., in order to remove the water, petrol ether and volatile impurities.

The yield of complex esters is quite low after such elaborate cleansing operations.

It is an aim of the present invention to remove the disadvantages of the prior art, and to provide a completely new method for the production and purification of complex esters.

The invention is based on the concept that complex polyol esters can be produced with good yield, by using organic bases, in particular tertiary amines, to neutralize the acid components, and by extracting the impurities into an aqueous solution. The tertiary amine used comprises an amine according to the formula $R^1R^2R^3N$, wherein $R^1$, $R^2$, and $R^3$ independently represent alkyl groups, having 1–5 carbon atoms, and/or aryl groups, and $R^1$ and $R^2$ can together form a substituted or unsubstituted ring, having 5–10 carbon atoms.

More specifically, the technical solution according to the invention is mainly characterized by what is stated in the characterizing part of claim 1.

The separation of the viscous complex esters is significantly easier with the present method than with conventional neutralization methods employing $NaHCO_3$, $Na_2CO_3$ or NaOH, or using hot neutralization. The amines are basic, but they do not directly react with the carboxylic acids, instead they form salt-like complexes. These enter the aqueuos phase, from which they are easily separated. The amines do not as easily form emulsions as strong inorganic bases do, and no solvents are necessarily needed for the cleansing.

In the following the invention will be discussed with the aid of a detailed description and some working examples. The enclosed figures show the LC product analysis according to Example 2 and the HPGPC product analysis of the product of Example 6.

This invention concerns in particular the manufacture of polyol-based complex esters in the case when the polyol is a sterically hindered, alpha-substituted diol, such as 2-butyl-2-ethyl-1,3-propanediol (BEPD), neopentyl glycol COPG), hydroxypivalyl hydroxypivalate (HPHP), or a triol, such as trimethylolpropane (IMP), trimethylolethane (TME) or pentaerythritol (PE). An important advantage of these sterically hindered polyols is their stability, which is important both for lubricant and refrigerant applications.

Mono- and polybasic carboxylic acids are used for the manufacturing of esters. Preferred carboxylic acids according to the invention are mixtures of $C_5$–$C_{18}$ monocarboxylic and dicarboxylic acids. The monocarboxylic acids may be either linear or branched, hydroxy acids (that is, they contain both a carboxylic and hydroxylic group) or they can contain double bond(s) (unsaturated).

Suitable monocarboxylic acids are for instance octanoic acid and 2-ethylhexanoic acid. A suitable hydroxy acid is hydroxypivalic acid (HPAA) and oleic acid can be mentioned as an unsaturated acid.

Examples of dicarboxylic acids are oxalic acid, malonic acid, dimethyhnalonic acid, succinic acid, glutaric acid, adipic acid, sebacic acid, pimelic acid, suberic acid and azelaic acid. Preferred dicarboxylic acids are adipic acid, sebacic acid and azelaic acid. Furthermore the carboxylic acid can be a mixture of one or several of the acids mentioned above together with dimethylmalonic acid or a cyclic anhydride, such as alkenyl succinic acid, or trimellitic anhydride.

In the method according to the invention all the reactants (polyol, catalyst, mono- and dicarboxylic acid) are weighed into the reactor and heated for 3–10 h, preferably 5–8h at 180–240° C., preferably at 200–220° C., until the acid number has decreased below 10 mg KOH/g. The molar ratio of the reactant di- and monoacids is in the range 5:95–40:60 mol %, typically 10:90–30:70 mol %. The esterification is preferably done by using catalyst acids, such as p-toluenesulphonic acid, sulphuric acid, hydrochloric acid, or metal oxides, such as titanates or tin oxides. The amount of catalyst used is typically 0.05–0.5% of the reacting components.

Since the esterization reaction is a condensation reaction, in which water is released, a low flow of protective gas (e.g. nitrogen) is maintained in order to make the removal of water more effective. Most preferably the protective gas is bubbled through the reaction mixture.

As a medium for the esterization an organic solvent can be used, which is inert with respect to the reactants, for example hydrocarbon with low boiling temperature, such as heptane, or a hydrocarbon mixture with high boiling temperature, such as LIAV 270. The solvent is added at the same time as the other reagents to the reactor. The amount of solvent is ca 10–50 weight-%, preferably ca 20–40 weight-% of the reactants.

After the reaction has come to an end the catalyst is filtered away. The filtering is preferably done when the reaction mixture is still hot, because filtering is then easier.

To neutralize the remaining acid, an amine is added to the cooled reaction mixture. The amine has the formula $R^1R^2R^3N$, wherein $R^1$, $R^2$ and $R^3$ represent independent alkyl groups, with 1–5 carbon atoms, or aryl groups; and $R^1$ and $R^2$ may together form a substituted or unsubstituted ring with 5–10 carbon atoms. Preferably $R_1$ and $R^2$ represent lower alkyl groups, such as methyl and ethyl, whereby especially preferred amines are trimethylamine and triethylamine. Other tertiary amines are tri-n-propylamine, tri-n-butylamine, tri-isobutylamine, tri-n-amylamine, triisoamylamine and methyl diethylamine. Examples or aromatic amines to be mentioned are dimethylaniline, triphenylamine, diethylaniline and ethylbenzylaniline.

The amount of amine fed into the reaction mixture is ca 0.1–30 weight-%, preferably ca 0.5–15 weight-%, in particular ca 1–10 weight-% (for example ca 2–5 weight-%). Thereafter the mixture is blended at 20–100° C., preferably at 60–90° C., for a suitable length of time. The blending time varies with the amount of acid components, typically from a couple of minutes to several hours. Usually the mixing takes ca 1–10 h.

According to a preferred embodiment, an organic solvent is used for the washing. The solvent promotes the separation and allows for a further increase of the yield. For the washing a similar solvent can be used as in the esterification reaction, that is for example an organic solvent with low boiling temperature, such as heptane, or a hydrocarbon mixture with high boiling temperature. If an organic solvent with low boiling temperature is used in the washing phase, the solvent is added to the reaction mixture before the base. The amount of solvent is 10–50 weight-%, most preferably 20–40 weight-% of the reactants.

After the alkaline washing, the impurities are extracted with water. Thus, water is added to the neutralized mixture in such a way that the amount of water is at least about the same as that of the base, that is ca 0.1–30 weight-%, preferably ca 0.5–15 weight-% of the reaction mixture. The amine-carboxylic acid complex or salt formed in the neutralizing reaction is separated and the emulsion that may have been formed is salted out with NaCl-solution. After this the reaction mixture is washed with dilute mineral acid (for example ca 0.5–2 M hydrochloric or phosphoric acid) and thereafter once or twice with warm water. The final product is dried with a drying agent, for example, on sodium sulphate, and filtered. If a solvent has been used, it is removed with vacuum distillation (2–3 h, 1 mbar, 200–230° C.) after washing with water, and filtered.

The following examples illustrate the method according to the invention. In Examples 1–31 2-butyl-2thyl-1,3-propanediol has been used as polyol, and in Examples 32–38 neopentyl glycol, trimethylolpropane, hydroxypivalyl hydroxypivalate and pentaerythritol. In Example 4 a solvent has been added in the cleansing phase.

Examples 1–3 and 5–31

Complex esters of BEPD (2-butyl-2-ethyl-1,3-propanediol) were manufactured by loading the reactor vessel with BEPD and saturated linear or branched monocarboxylic acid ($C_{5-C6}$) or unsaturated carboxylic acid ($C_{14-C22}$) and diacid (adipic, sebacic), whereby 1 mol % of monoacid was used in excess of alcohol. The amount of the tin oxide catalyst (Tekokat 188) was 0.15 weight-% of the amount of reagent. The reaction blend was heated to 200–220° C. in nitrogen atmosphere and was kept at this temperature for ca 7 hours, or until the acidity had decreased below 10 mg KOH/g. After the blend had been cooled, an organic base (triethylamine) was added at an amount of 5–15 weight-% of the amount of reagens. The blend was heated to 80° C. and mixed for ca 3 hours. The blend was washed once or twice with a small amount of water (base:water 1:1). Excess base was washed away with 0.5–1.0 M mineral acid (HCl, $H_3PO_4$). Eventually the blend was washed once or twice with water and dried with $Na_2SO_4$.

The products obtained with different acids and varying molar ratios are presented together with their properties in Tables 1–10 and a typical LC-product analysis of the product according to Example 2 is presented in FIG. 1.

Example 4

The reactants (BEPD, catalyst, adipic acid and octanoic acid and solvent) were measured into a retort and heated for 7 h 200–220° C. A low flow of nitrogen was maintained in order to make the removal of water more efficient. A solvent mixture (LIAV 270) with high boiling temperature was used for solvent, its amount was 30% of the reactants. After the reaction had come to its end, the catalyst was filtered away while the reaction blend was still hot. After the reaction mixture had cooled, 3 weight-% triethylamine was added, and the mixture was blended for ca 3 hours at 70–80° C.

After purification of the base, water was added at the same amount as base. The salt that had formed was separated and the emulsion that might have formed was salted out with NaCl-solution. Thereafter the reaction blend was washed with dilute HCl and twice with warm water. The end-product was dried with $Na_2SO_4$ and filtered.

The properties of the product are presented in Table 1 (Example 4).

Examples 32–38

The reaction was performed as in the Examples 1–3 and 5–31, with the distinction that the polyol used was NPG, TMP, HPHP or PE.

Tables 1–4. Properties of BEPD Complex Esterm

TABLE 1

| BEPD + adipic acid + octanoic acid | | | | | | |
|---|---|---|---|---|---|---|
| Example No./ acid mol-% | $V_{100}$ mm$^2$/s | $V_{40}$ mm$^2$/s | VI | PP ° C. | Acid No. mg KOH/g | Yield % |
| 1. 10/90 | 3.84 | 17.4 | 112 | −60 | 0.05 | 71 |
| 2. 20/80 | 5.33 | 28.2 | 125 | −54 | 0.3 | 58 |
| 3. 30/70 | 7.54 | 47.3 | 124 | −45 | 1.9 | 36 |
| 4.* 30/70 | 7.51 | 44.9 | 133 | −42 | 0.79 | 69 |

*solvent 30 weight % (LIAV 270)

TABLE 2

| BEPD + adipic acid + nonanoic acid | | | | | | |
|---|---|---|---|---|---|---|
| Example No./ acid mol-% | $V_{100}$ mm$^2$/s | $V_{40}$ mm$^2$/s | VI | PP ° C. | Acid No. mg KOH/g | Yield % |
| 5. 10/90 | 4.30 | 20.2 | 121 | −57 | 1.0 | 72 |
| 6. 20/80 | 5.78 | 31.8 | 125 | −51 | 1.0 | 65 |
| 7. 30/70 | 8.43 | 53.5 | 131 | −51 | <0.1 | 41 |

TABLE 3

BEPD + adipic acid + decanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 8. 10/90 | 4.83 | 23.1 | 134 | −54 | 1.1 | 79 |
| 9. 20/80 | 6.59 | 36.5 | 137 | −54 | 0.93 | 60 |
| 10. 30/70 | 9.28 | 60.5 | 133 | −48 | 3.3 | 54 |

TABLE 4

BEPD + adipic acid + dodecanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 11. 10/90 | 5.90 | 30 | 145 | — | 2.2 | 43 |
| 12. 20/80 | 6.3 | 34.9 | 132 | −39 | 0.14 | 56 |
| 13. 30/70 | 10.4 | 68.4 | 139 | −36 | 1.0 | 53 |

TABLE 5

BEPD + adipic acid + oleic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 14. 10/90 | 8.04 | 41.1 | 173 | −39 | 1.4 | 74 |
| 15. 20/80 | 9.88 | 54.0 | 172 | −42 | 0.9 | 59 |
| 16. 30/70 | 11.9 | 72.1 | 161 | −42 | 0.35 | 66 |

TABLE 6

BEPD + sebacic acid + octanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 17. 10/90 | 4.32 | 20.0 | 124 | −60 | 0.6 | 76 |
| 18. 20/80 | 6.66 | 36.5 | 140 | −54 | 1.56 | 63 |
| 19. 30/70 | 10.6 | 68.7 | 142 | −54 | 2.1 | 55 |

TABLE 7

BEPD + sebacic acid + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 20. 10/90 | 4.76 | 22.8 | 132 | −60 | 1.3 | 78 |
| 21. 20/80 | 7.16 | 40.0 | 143 | −54 | 1.9 | 68 |
| 22. 30/70 | 9.41 | 64.4 | 125 | −51 | 1.6 | 62 |

TABLE 8

BEPD + sebacic acid + decanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 23. 10/90 | 5.31 | 25.9 | 143 | −54 | 1.6 | 69 |
| 24. 20/80 | 7.78 | 44.2 | 147 | −51 | 2.6 | 56 |
| 25. 30/70 | 7.22 | 41.6 | 137 | −45 | 1.3 | 48 |

TABLE 9

BEPD + sebacic acid + dodecanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 26. 10/90 | 6.98 | 37.1 | 152 | −27 | 2.3 | 57 |
| 27. 20/80 | 9.05 | 52.8 | 153 | <−30 | 1.0 | 61 |
| 28. 30/70 | 13.1 | 87.5 | 149 | −36 | 2.7 | 51 |

TABLE 10

BEPD + sebacic acid + oleic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 29. 10/90 | 8.61 | 43.7 | 180 | −39 | 2.4 | 71 |
| 30. 20/80 | 11.2 | 62.5 | 174 | −39 | 2.2 | 55 |
| 31. 30/70 | 15.2 | 94.9 | 169 | <−30 | 2.8 | 29 |

Tables 11–13. Properties of other polyol complex esters.

TABLE 11

NPG + adipic acid + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 32. 20/80 | 4.47 | 19.0 | 155 | <−30 | 1.6 | 64 |

TABLE 12

NPG + sebacic acid + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 33. 20/80 | 5.75 | 25.5 | 179 | <−39 | 0.8 | 59 |

TABLE 13

HPHP + adipic acid + octanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 34. 20/80 | 7.06 | 39.8 | 140 | −51 | 1.0 | 66 |

TABLE 14

HPHP + sebacic acid + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 35. 20/80 | 8.79 | 50.5 | 154 | −51 | 0.15 | 62 |

TABLE 15

TMP + adipic acid + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 36. 20/80 | 13.6 | 92.2 | 149 | −45 | 0.57 | 68 |

TABLE 16

TMP + adipic acid + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 37. 20/80 | 19.3 | 135.9 | 162 | −45 | 0.8 | 45 |

TABLE 17

PE + adipic + nonanoic acid

| Example No./ acid mol-% | $V_{100}$ mm²/s | $V_{40}$ mm²/s | VI | PP °C. | Acid No. mg KOH/g | Yield % |
|---|---|---|---|---|---|---|
| 38. 10/90 | 12.9 | 86.9 | 147 | <−30 | 0.36 | 59 |

What is claimed is:

1. A process for the production of complex polyol ester with high yield, which comprises:
   reacting a polyol with mono- and polybasic acids in the presence of a catalyst to produce a reaction blend containing complex esters,
   treating the reaction blend with a base to neutralize the acid components in the reaction blend, wherein the base is comprised of a tertiary amine in an organic solvent and the tertiary amine has the formula $R^1R^2R^3N$, wherein $R^1$, $R^2$ and $R^3$ represent independent alkyl groups with 1–5 carbon atoms, and aryl groups, and $R^1$ and $R^2$ can together form a substituted or unsubstituted ring with 5–10 carbon atoms, and
   recovering the complex esters from the reaction blend treated in this manner.

2. The process according to claim 1, wherein the amount of organic solvent is ca 10 to 50 weight-% of the reaction blend.

3. The process according to claim 1, wherein the tertiary amine used is an aliphatic amine or an aromatic amine.

4. The process according to claim 1, wherein water is added to the reaction blend after the amine treatment and the salts thus formed are separated.

5. The process according to claim 4, wherein the amount of water is 0.1 to 30 weight-% of the reaction blend.

6. The process according to claim 4, wherein the reaction blend is washed and the complex esters are recovered by separating the solid impurities and the solvent, if present, from the reaction blend.

7. The process according to claim 1, wherein the polyol is a sterically hindered, alpha-substituted diol or a triol.

8. The process according to claim 1, wherein the carboxylic acid is a mixture of $C_5$–$C_{18}$ monocarboxylic acids and dicarboxylic acids.

9. The process according to claim 8, wherein the monocarboxylic acid is linear or branched, a hydroxy acid or it contains a double bond.

10. The process according to claim 9, wherein the monocarboxylic acid is octanoic acid, 2-ethylhexanoic acid, hydroxypivalic acid or oleic acid.

11. The process according to claim 8, wherein the dicarboxylic acid is oxalic acid, malic acid, dimethylmalic acid, succinic acid, glutaric acid, adipic acid, sebacic acid, pimelic acid, suberic acid or azelaic acid, or a cyclic anhydride or an alkyl derivative thereof, or trimellitine anhydride.

12. The process according to claim 8, wherein the molar ratio of di- and monoacids is in the range from 5:95 to 40:60 mol-%.

13. The process according to claim 1, wherein the amount of catalyst used is 0.05–0.5% of the total amount of the polyol, the mono- and polybasic acids and the catalyst.

14. The process according to claim 13, wherein the catalyst used is an acid catalyst or metal oxide.

15. The process according to claim 1, wherein the reaction time of the esterification is 3–10 h, at 180–240° C., in order to reduce the acid number below 10 mg KOH/g.

16. The process according to claim 1, wherein the solvent used in the reaction phase is a non-polar hydrocarbon or a hydrocarbon mixture with high boiling temperature.

17. The process according to claim 1, wherein 2 to 5 weight-% tertiary amine is added to the reaction blend.

18. The process according to claim 1, wherein the reaction blend is treated with tertiary amine at a temperature in the range of 20 to 100° C.

19. The process according to claim 3, wherein the aliphatic amine is selected from the group consisting of trimethylamine, triethylamine, tri-n-propylamine, tri-n-butyl-amine, triisobutylamine, tri-n-amylamine, triisoamylamine and methyl-diethylamine.

20. The process according to claim 3, wherein the aromatic amine is selected from the group consisting of dimethylaniline, triphenylamine, diethylaniline and ethylbenzylaniline.

21. The process according to claim 7, wherein the sterically hindered, alpha-substituted diol is 2-butyl-2-etyl-1,3-propanediol, neopentyl glycol or hydroxypivalyl hydroxypivalate.

22. The process according to claim 7, wherein the triol is trimethylolpropane, trimethylol ethane or pentaerythritol.

23. The process according to claim 11, wherein the cyclic anhydride is succinic anhydride.

24. The process according to claim 12, wherein the molar ratio of di- and monoacids is in the range of 10:90–30:70 mol %.

25. The process according to claim 14, wherein the acid catalyst is p-toluene-sulphonic acid, sulphuric acid or hydrochloric acid.

26. The process according to claim 14, wherein the metal oxide is tin oxide or titanate.

27. The process according to claim 15, wherein the reaction time of esterification is 5–8 h.

28. The process according to claim 16, wherein the non-polar hydrocarbon is heptane.

* * * * *